United States Patent [19]

Shoesmith, deceased

[11] Patent Number: Plant 5,943

[45] Date of Patent: Apr. 14, 1987

[54] CHRYSANTHEMUM PLANT NAMED FASCINATION

[75] Inventor: Leonard H. Shoesmith, deceased, late of Westfield, England, by May V. Shoesmith, executrix

[73] Assignee: Ball Pan Am Plant Company, Parrish, Fla.

[21] Appl. No.: 746,980

[22] Filed: Jun. 20, 1985

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Fascination having flat capitulum form and spoon tipped daisy type; lavender ray floret color; diameter of 1" to 2.5" across face of flower; uniform eight week flowering response using photoperiodic control and when grown in a 6" pot with its center bud removed.

1 Drawing Figure

The present invention comprises a new and distinct cultivar of *Chrysanthemum morifolium,* Ramat., hereinafter referred to by the cultivar name Fascination.

Fascination is a product of a planned breeding program which had the objective of creating new Chrysanthemum cultivars with novelty flower forms, early response, and having the ability to be grown in year around programs. Such traits in combination were not present or needed improvement in previously available commercial cultivars.

Fascination was originated from a hybridization made in a controlled breeding program by Leonard H. Shoesmith in Westfield, Woking, Great Britain in 1979. The male and female parents are unknown at this time.

Fascination was discovered and selected as one flowering plant within the progeny of the stated parentage by or under the supervision of Leonard H. Shoesmith in November of 1979 in a controlled environment in West Chicago, Ill., and given the code #P9-1215-PS.

The first act of asexual reproduction of Fascination was accomplished when vegetative cuttings were taken from the initial selection in February of 1980 in a controlled environment in West Chicago, Ill. by a technician working under formulations established and supervised by Leonard H. Shoesmith. Horticultural examination of selected units initiated February of 1980 has demonstrated that the combination of characteristics as herein disclosed for Fascination are firmly fixed and are retained through successive generations of asexual reproduction.

Fascination has not been observed under all possible environmental conditions. The phenotype may vary significantly with variations in environment such as temperature, light intensity and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Fascination which in combination distinguish this Chrysanthemum as a new and distinct cultivar:

(1) Flat capitulum form.

(2) Spoon tipped daisy type under cool temperatures, changing to a more flat petalled daisy under high temperature.

(3) Ray floret color is medium lavender at cool temperatures, but fades to a very light lavender at extremely high temperatures.

(4) Diameter across face of flower is 1" to 2.5".

(5) Uniform 8 week flowering response using photoperiodic control, when grown in a 6" pot with its center bud removed.

(6) Height is 12" to 18" above edge of a 6" pot; height is dependent on time of bud initiation and temperature.

Of the many commercial cutivars known to the present inventor, the most similar in comparison to Fascination is Fantasy. In comparison to Fantasy, Fascination has a lighter color, a more quilled flower type, and is less sensitive to temperature extremes, both high and low. The flower form and plant habit are similar to those same characteristics of Fantasy.

The accompanying photographic drawing shows typical inflorescence and foliage characteristics of Fascination. The photograph is in black and white except for a cluster of flowers which represent the true flower color of Fascination.

In the following description, color references are made to The Royal Horticultural Society Colour Chart. The color values were determined at approximately 12:00 noon on May 2, 1985 under inflorescent light at Bradenton, Fla.

Classification:

*Botanical.*—*Chrysanthemum morifolium,* Ramat., cv Fascination.

*Commercial.*—Pot mum with center bud removed.

I. INFLORESCENCE

A. Capitulum:

*Form.*—Flat.

*Type.*—Spoon tipped, single.

*Diameter across face.*—1" to 2.5".

B. Corolla of ray florets:

*Color (general tonality from a distance of three meters).*—Lavender.

*Color (upper surface).*—77B-C; spoon tip 77B.

*Color (under surface).*—77B-C.

C. Corolla of disc florets:

*Color (mature).*—Yellow.

*Color (immature)*—Yellow.

D. Reproductive organs:

*Androecium.*—Present in disc florets only; insignificant.

*Gynoecium.*—One per both ray and disc floret.

II. PLANT

A. General appearance:

*Height.*—12" to 18" above the edge of a 6" pot.

B. Foliage:

*Color (upper surface).*—147A.

*Color (under surface).*—147B.

*Shape.*—Deeply lobed, margin repand.

It is claimed:

1. A new and distinct cultivar of Chrysanthemum plant named Fascination, as described and illustrated, and particularly characterized by its flat capitulum form and spoon tipped daisy type; lavender ray floret color; diameter of 1" to 2.5" across face of flower; uniform eight week flowering response using photoperiodic control and when grown in a 6" pot with its center bud removed.

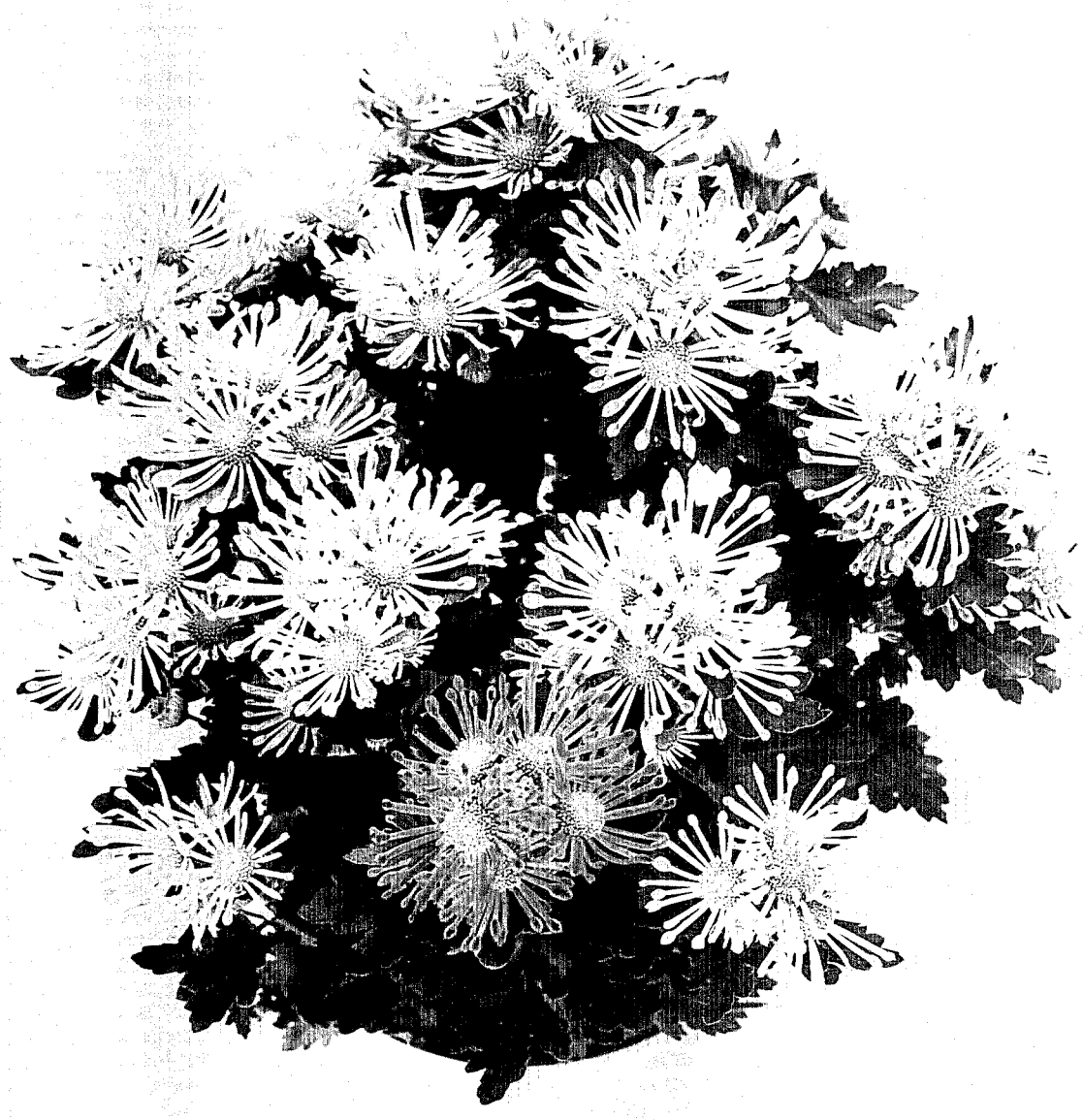

* * * * *